United States Patent
Lewis et al.

(10) Patent No.: US 7,344,273 B2
(45) Date of Patent: Mar. 18, 2008

(54) RING LIGHT WITH USER MANIPULABLE CONTROL

(75) Inventors: Walter F. Lewis, Overland, MO (US); Leonard R. Missler, Chesterfield, MO (US)

(73) Assignee: Binary Works, Inc., Chesterfield, MO (US)

( * ) Notice: Subject to any disclaimer, the term of this patent is extended or adjusted under 35 U.S.C. 154(b) by 0 days.

(21) Appl. No.: 11/085,990

(22) Filed: Mar. 22, 2005

(65) Prior Publication Data

US 2006/0215400 A1  Sep. 28, 2006

(51) Int. Cl.
*F21V 21/15* (2006.01)

(52) U.S. Cl. ............... 362/233; 362/235; 362/800; 345/163

(58) Field of Classification Search ............ 362/233, 362/250, 251, 297, 276, 234, 235, 800, 466, 362/464, 458, 85, 295; 345/166, 165, 163, 345/156, 157; 359/383–390
See application file for complete search history.

(56) References Cited

U.S. PATENT DOCUMENTS

| | | |
|---|---|---|
| 1,444,400 A | 2/1923 | Silverman |
| 1,873,149 A | 8/1932 | Perez |
| 2,144,653 A | 1/1939 | Graff |
| 2,409,328 A | 10/1946 | Wilder |
| 3,903,363 A | 9/1975 | Montone et al. |
| 3,930,713 A | 1/1976 | Stankewitz et al. |
| 4,025,777 A | 5/1977 | Hayakawa |
| 4,028,728 A | 6/1977 | Sharp |
| 4,293,219 A | 10/1981 | Ducloux |
| 4,567,551 A | 1/1986 | Choate |
| 4,604,648 A | 8/1986 | Kley |
| 4,622,625 A | 11/1986 | Becker et al. |
| 4,677,473 A | 6/1987 | Okamoto et al. |
| 4,706,168 A | 11/1987 | Weisner |
| 4,729,079 A | 3/1988 | Maylotte |
| 4,737,845 A | 4/1988 | Susuki et al. |
| 4,847,911 A | 7/1989 | Morimoto et al. |
| 4,881,802 A | 11/1989 | Stankewitz |
| 4,882,498 A | 11/1989 | Cochran et al. |
| 4,884,008 A | 11/1989 | Bossler et al. |
| 4,894,677 A | 1/1990 | Bourcier et al. |
| 4,963,798 A | 10/1990 | McDermott |
| 4,972,093 A | 11/1990 | Cochran et al. |
| 5,030,008 A | 7/1991 | Scott et al. |
| 5,051,825 A | 9/1991 | Cochran et al. |
| 5,060,065 A | 10/1991 | Wasserman |
| 5,113,565 A | 5/1992 | Cipolla et al. |
| 5,247,344 A | 9/1993 | Doan |
| 5,257,714 A | 11/1993 | Beers et al. |
| 5,369,492 A | 11/1994 | Sugawara |
| 5,394,246 A | 2/1995 | Sugawara |
| 5,420,689 A | 5/1995 | Siu |

(Continued)

*Primary Examiner*—Sandra O'Shea
*Assistant Examiner*—Bao Q. Truong
(74) *Attorney, Agent, or Firm*—Polster, Lieder, Woodruff & Lucchesi LC

(57) ABSTRACT

An illumination device having a plurality of light sources, a user manipulable control and a circuit. The circuit receives an input from the user manipulable control, determines an illumination angle of the plurality of light sources based upon the input, and illuminates at least one of the light sources such that the light sources are illuminated in accordance with the illumination angle.

28 Claims, 4 Drawing Sheets

U.S. PATENT DOCUMENTS

| | | |
|---|---|---|
| 5,424,838 A | 6/1995 | Siu |
| 5,446,825 A | 8/1995 | Moslehi et al. |
| 5,455,870 A | 10/1995 | Sepai et al. |
| 5,576,828 A | 11/1996 | Tomiyama et al. |
| 5,580,163 A | 12/1996 | Johnson, II |
| 5,690,417 A * | 11/1997 | Polidor et al. ............... 362/244 |
| 5,774,212 A | 6/1998 | Corby, Jr. |
| 5,820,250 A | 10/1998 | Betts et al. |
| 5,828,449 A | 10/1998 | King et al. |
| 5,892,539 A | 4/1999 | Colvin |
| 5,897,195 A | 4/1999 | Choate |
| 5,920,643 A | 7/1999 | White et al. |
| 5,926,557 A | 7/1999 | King et al. |
| 5,943,125 A | 8/1999 | King et al. |
| 5,984,493 A | 11/1999 | Higgins et al. |
| 5,997,164 A | 12/1999 | Betts et al. |
| 6,017,133 A | 1/2000 | Grasmuller et al. |
| 6,070,986 A | 6/2000 | Yoneda |
| 6,120,164 A | 9/2000 | Libin et al. |
| 6,141,046 A | 10/2000 | Roth et al. |
| 6,238,060 B1 * | 5/2001 | Bourn et al. ................ 362/216 |
| 6,273,338 B1 | 8/2001 | White |
| 6,385,507 B1 | 5/2002 | Buijtels |
| 6,454,437 B1 * | 9/2002 | Kelly ......................... 362/246 |
| 6,456,431 B2 | 9/2002 | Yamahiro |
| 6,533,429 B2 | 3/2003 | Yoneda |
| 6,554,452 B1 | 4/2003 | Bourn et al. |
| 6,621,569 B2 | 9/2003 | Sones |
| 6,633,338 B1 | 10/2003 | Pelsue et al. |
| 6,683,421 B1 | 1/2004 | Kennedy et al. |
| 6,769,790 B2 * | 8/2004 | Fruhm et al. ............... 362/286 |
| 6,774,893 B2 | 8/2004 | Debiez et al. |
| 2003/0081410 A1 * | 5/2003 | Bailey ....................... 362/147 |
| 2005/0030744 A1 * | 2/2005 | Ducharme et al. .......... 362/231 |

* cited by examiner

RING LIGHT WITH USER MANIPULABLE CONTROL

FIELD OF THE INVENTION

This invention relates generally to optical system illumination, and more particularly to ringlights for the purpose of illumination of objects under examination by a human operator under a microscope, video camera, magnifier, or similar device.

BACKGROUND OF THE INVENTION

Optical viewing and imaging systems require some form of illumination of the object under examination for such purposes as viewing by a human operator, photography of the object, or for machine vision analysis. The ring illumination technique has long been used to provide a good source of even illumination. For example, U.S. Pat. No. 1,444,400 issued in 1923 describes a ringlight using a circular incandescent light bulb.

Fluorescent ring lamps are commonly used today for ringlight systems, as utilized for instance in U.S. Pat. No. 5,247,344. Other techniques for distributing light in a ringlight system have been employed, such as the use of fiber optics, lenses, mirrors, shutters, and prisms, each with their respective benefits and drawbacks. A common feature of these types of ringlight systems is the use of a single, or limited number of light generating sources, which limits the ability to alter the light characteristics under electrical control.

With the advent of inexpensive light emitting diodes (LEDs) has come the use of arrays of LEDs in ringlights. U.S. Pat. Nos. 6,554,452, 6,454,437, 6,141,046, 5,997,164, 5,943,125, 5,926,557, 5,892,539, 5,828,449, 5,820,250, 5,580,163, 4,963,798, and 4,881,802, all include ringlights fashioned from a ring of LEDs. In a refinement of the LED ring concept, multiple concentric rings of LEDs allow selectable angles of inclination of the LED illumination relative to the optical axis by selectively energizing one LED ring or another. Such refinements are described in U.S. Pat. Nos. 6,385,507, 6,238,060, 6,070,986, 5,920,643, 5,576,828, and 5,030,008. In a further refinement, individual LEDs or groups of LEDs within a given single ring allow selectable direction of the LED illumination rotationally around the optical axis by up to 360 degrees. Such ring illumination systems are described in U.S. Pat. Nos. 6,017,133, 5,897,195, 5,690,417, 5,394,246, 5,369,492, and 5,060,065.

The control of these illumination systems varies according to the purpose of the system. For instance, machine vision and process control systems typically use a computer to adjust the lighting as necessary to satisfy a set of recognition criteria. Examples of such systems include U.S. Pat. Nos. 6,774,893, 6,633,338, 6,238,060, 6,017,133, 5,943, 125, 5,926,557, 5,828,449, 5,455,870, 5,424,838, 5,420,689, 5,394,246, 5,369,492, 5,030,008, 4,972,093, 4,882,498, 4,706,168, and 4,604,648.

Other illumination systems specify variations on the LED mounting and optical path configuration but do not specify any type of machine or operator control mechanism. Examples of such systems include U.S. Pat. Nos. 6,533,429, 6,385,507, 5,690,417, 5,897,195, 6,273,338, 5,774,212, and 5,060,065.

It is thus apparent that there exists a need for improved control mechanisms that can utilize the various features of the available prior art solutions discussed above.

SUMMARY OF THE INVENTION

The present invention provides an illumination device comprising a plurality of light sources, a user manipulable control and a circuit. The circuit receives an input from the user manipulable control, determines an illumination angle of the plurality of light sources based upon the input, and illuminates at least one of the light sources such that the light sources are illuminated in accordance with the illumination angle.

DETAILED DESCRIPTION OF THE PREFERRED EMBODIMENT

Figure 1:
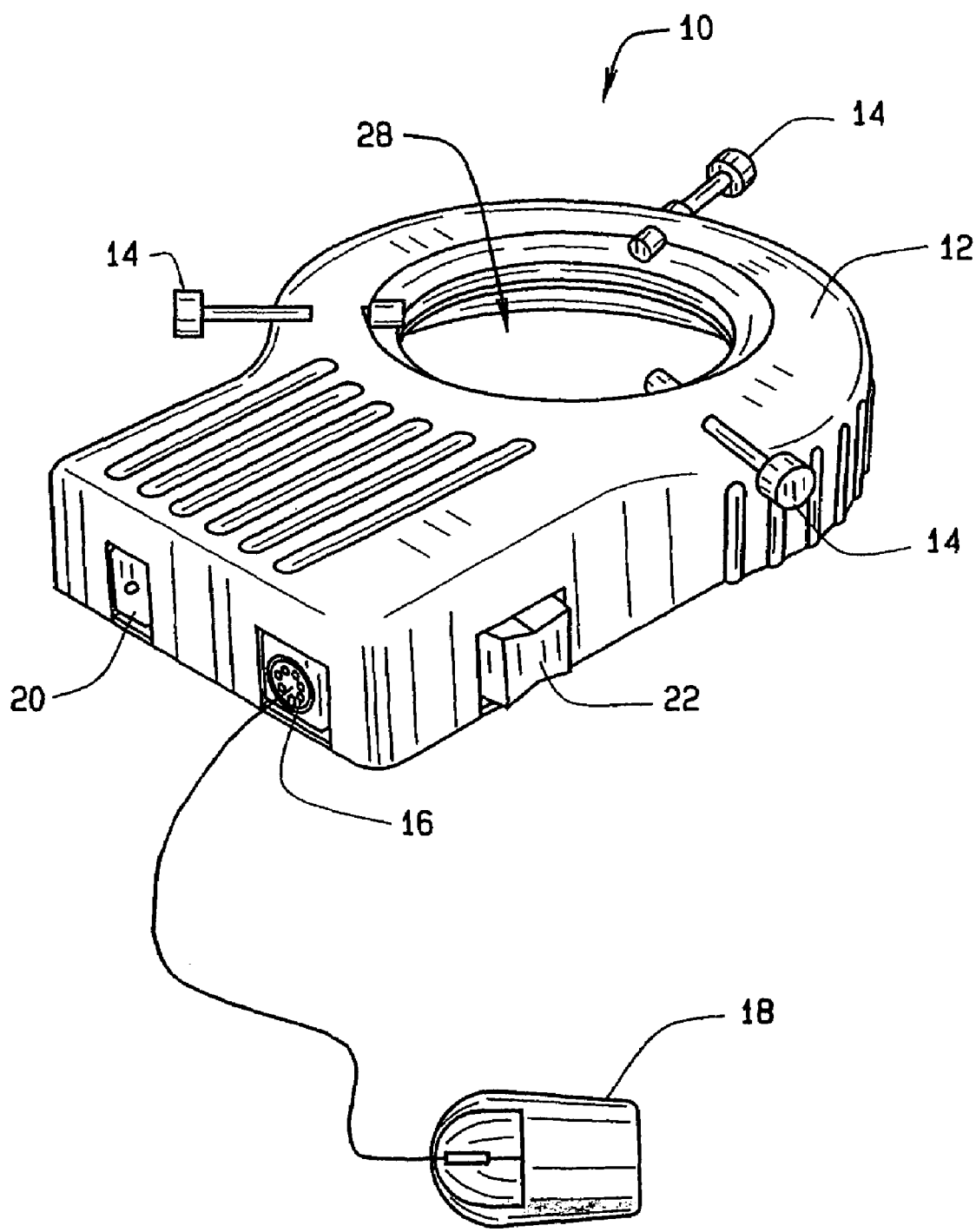
FIG. 1 is a perspective view of a ringlight and mouse according to an embodiment of the present invention.

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

Disclosed is a ringlight system for illumination of objects under a microscope, magnifying lamp or video camera, and includes circuitry for controlling intensity, rotation angle, rotation rate, and directionality of the light source using a manipulable device, most preferably a standard computer mouse. The system comprises a circular array of densely spaced LEDs arranged in a plane perpendicular to the optical axis. The centerline of each LED beam is angled such that all LED centerlines intersect the optical axis at a common point. In the most preferred embodiment, a mouse port emulator circuit disposed in the ringlight emulates the functions of a computer mouse port, enabling a computer mouse to be directly connected to the ringlight without the need for a computer. A rotation detection circuit takes mouse data and converts it to rotation direction and rotation speed information. An LED sequencer circuit takes rotation direction and rotation speed information from the rotation detection circuit as well as mouse wheel and mouse button data, and selectively energizes groups of LEDs as directed by the operator through circular motion of the mouse, rotation of a the mouse wheel and actuation of mouse buttons.

Each LED is independently controllable by said LED sequencer circuit, allowing illumination of the object under examination from any direction angle and with any degree of directionality. For instance a single LED could be energized, providing a highly directional source of illumination or a pie-shaped group of LEDs could be energized, providing a less directional source of illumination, or all LEDs could be energized, providing a 360 degree omni directional source of illumination. In one embodiment of the invention, circular motion of the mouse by the operator causes the pie shaped group of LEDs to rotate in a corresponding clockwise or counterclockwise manner, while rotation of the mouse wheel by the operator increases or decreases the number of LEDs energized in the pie shaped group.

Figure 2:
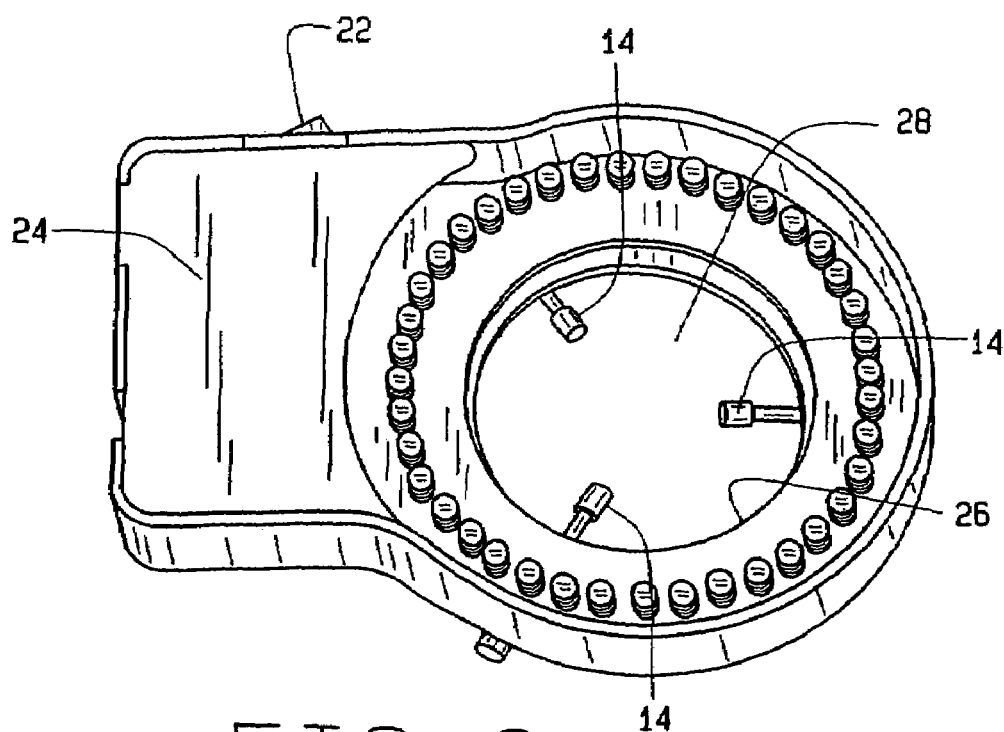
FIG. 2 is a bottom plan view of a ringlight according to an embodiment of the present invention.

In this regard and referring to FIGS. 1 and 2, there is provided a ringlight 10 according to an embodiment of the present invention. The ringlight 10 comprises a housing 12 having thumbscrews 14 threaded therethrough for mounting the ringlight 10 to a microscope, video camera, magnifier, or similar device, as is known in the prior art. The ringlight 10 further comprises a port 16 having a standard computer mouse 18 attached thereto and power input 20 for connecting to a source of electrical power. A switch 22 is disposed along the side of the ringlight 10. The switch 22 is preferably a three position rocker switch that can be operated to turn on the ringlight, turn off the ringlight, or when in the on position can be momentarily switched to the third position to sequentially initiate one or more predefined functions, such as preset illumination intensities, preset directionalities, or automatic illumination rotation, as further described below.

From the view of FIG. 2, an underside of the ringlight 10 can be seen. A cover 24 partially encloses a printed circuit board 26 having the electronic components of the printed circuit board thereon.

Figure 3:
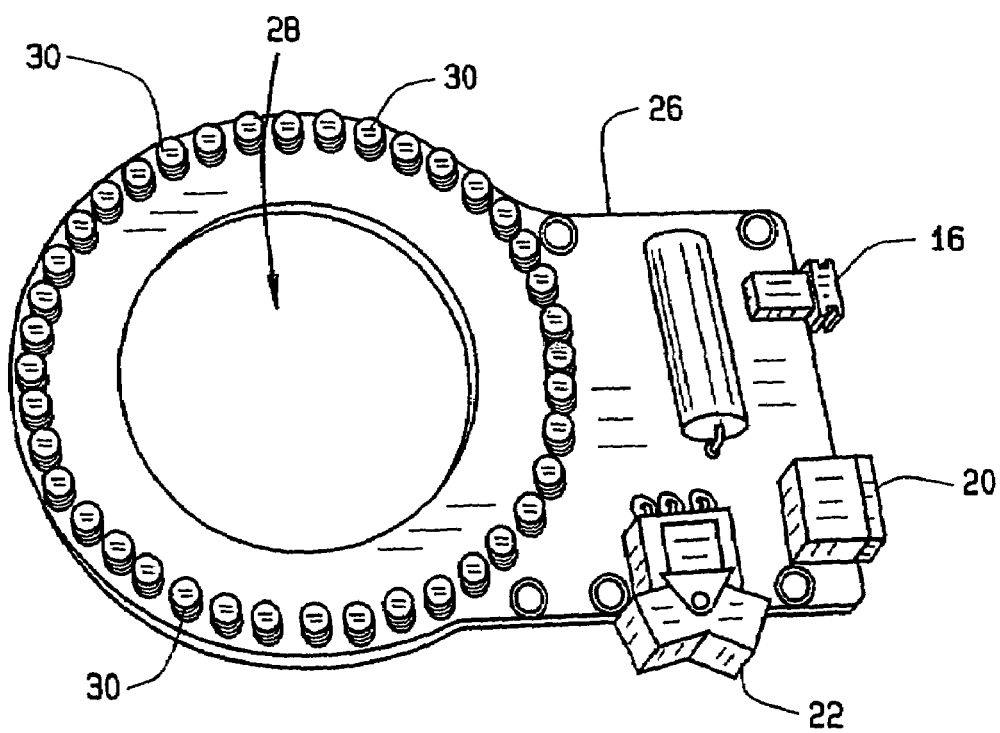
FIG. 3 is a top plan view of a printed circuit board according to an embodiment of the present invention.
Figure 4A:
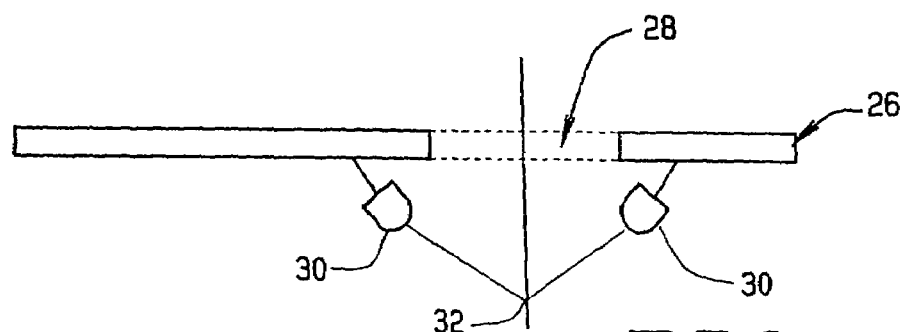
FIG. 4A is a diagrammatic view of a printed circuit board according to an embodiment of the present invention.
Figure 4B:
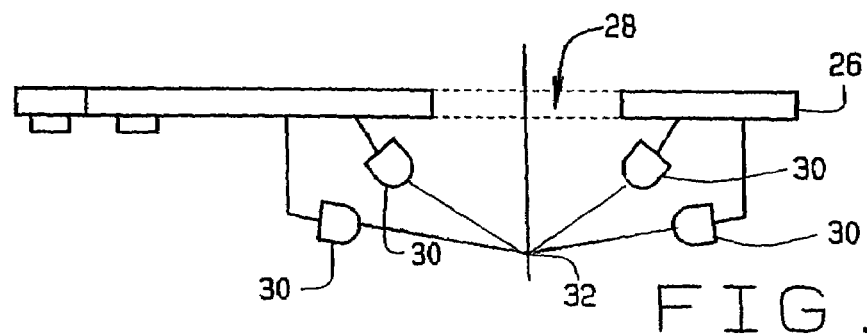
FIG. 4B is a diagrammatic view of a printed circuit board according to an embodiment of the present invention.

Referring to FIG. 3, the printed circuit board 26 of the present invention is shown. Attached to the printed circuit board 26 are the mouse port 16, power input 20 and the switch 22. As can be further seen, the printed circuit board 26 defines an opening 28 having a plurality of light sources 30 attached adjacent to a periphery of the opening 28. The light sources 30 are preferably light emitting diodes (LEDs). However, while white, visible light is the preferred source of light, other light sources that emit light of any frequency or frequencies, such as ultraviolet, infrared or visible light of any color could be used, and the LEDs may also be replaced with other types of sources such as common incandescent or fluorescent sources, without departing from the scope of the present invention. Preferably, the light sources 30 are attached to the printed circuit board 26 at an angle so that each light source 30 is substantially focused on a single focal point 32 below the opening 28 of the ringlight 10 (FIGS. 4A and 4B). Preferably, this is accomplished by arranging the light sources in a ring, although the light sources could be arranged in a linear array if desired. However, it should be understood that the for purposes of the present invention, the term "ring" refers to light sources arranged in a circular ring or a polygonal ring or a non-regular arrangement that generally forms a ring, such as a staggered arrangement shown in FIG. 4B.

Figure 5:
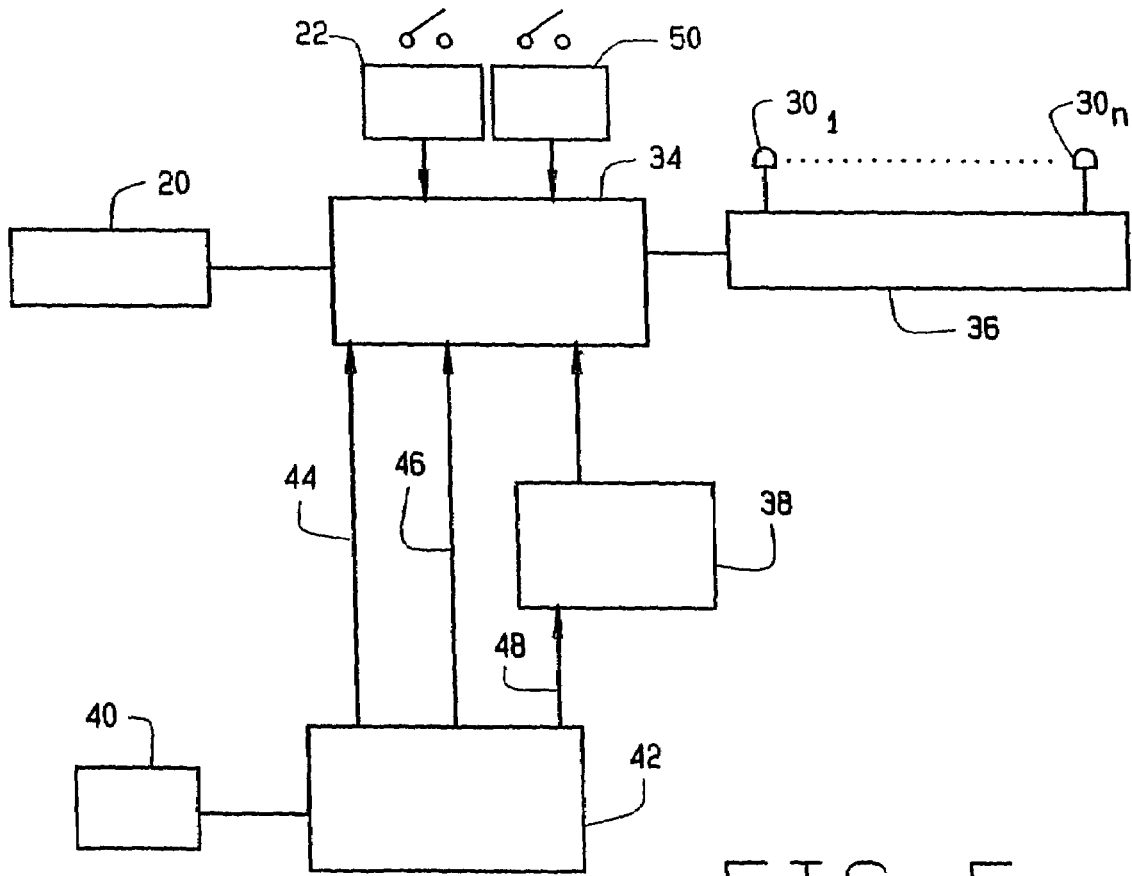
FIG. 5 is a diagrammatic view of a printed circuit board according to an embodiment of the present invention.

Referring to FIG. 5, the electrical components mounted to the printed circuit board 26 of the ringlight 10 are shown in diagrammatic form. Specifically, a light source sequencer 34 is provided and is electrically connected to the switch 22 and the power input 20. Also electrically connected to the light source sequencer 34 is a plurality of light sources $30_1$ to $30_n$ through a shift register/light source driver 36. The shift register/light source driver 36 receives a serial communication from the light source sequencer 34 that indicates which light sources $30_1$ to $30_n$ should and should not be illuminated and provides power only to the light sources 30 that should be illuminated. The light source sequencer 34 determines which should be illuminated by communicating with the device interpreter 38 that receives information from an externally-located hand manipulable user device 40, which in its preferred form is a standard computer mouse having a USB or PS/2 type interface. However, other devices could be used such as a trackball, joystick, touch pad, wireless mouse, digitizing pad, or foot manipulated control. The device interpreter 38 is shown as a separate device but could be included within the logic of the light source sequencer 34. Because the preferred embodiment of the invention implements a mouse as the hand manipulable user device 40, the preferred embodiment of the invention further includes a mouse port emulator 42 in communication with the light source sequencer 34 that communicates mouse click data on data line 44, mouse wheel movement data on data line 46, and raw mouse motion data on data line 48.

In this manner, the present ringlight is used (in the case of a mouse as the hand manipulable user device 40) by rotating the mouse to move the location along the ring of light sources 30 of the light sources 30 that are currently illuminated. By rolling the wheel on the mouse either direction, the user can increase or decrease the number of light sources 30 that are illuminated. By clicking the mouse, the user can select preset modes of illumination of the light sources.

When a PS/2 mouse communicates with a computer, it uses a half duplex bi-directional synchronous serial communication protocol. On power-up, the mouse runs a self-test and then sends a pass or fail indication to the computer. If the mouse passes the power-up self test then the computer goes through a negotiation protocol with the mouse to determine which mouse features are available, such as the number of buttons or the existence of a wheel. The computer then sends configuration information to the mouse which tells the mouse how to communicate and how frequently. The mouse can be configured to automatically send position and button status messages or only send status messages when requested by the computer. When configured to automatically send position and button status, the repetition rate at which status messages are sent is also configurable. Once the mouse has been configured, it is ready for use as an input device by the user. During use, the mouse sends status messages in the form of multi-byte data packets containing mouse motion information as well as button status and wheel rotation status. The motion information sent by the mouse consists of separate signed X and Y motion data representing the relative distance moved by the mouse in the right/left ($\pm X$) and forward-backward ($\pm Y$) directions since the last packet. Note that since the X and Y motion data represents relative changes in position, not absolute positions, and since this data is sent at regular time intervals, the X and Y values really represent velocities in the X and Y directions. Also within the packet are button status bits indicating the current state of each button, a logical 1 indicating button pressed or logical 0 indicating button released. If a mouse wheel exists, and if the mouse has been configured by the computer to utilize it, then wheel motion information is included in the packet as a signed value representing the relative distance the wheel has been rotated since the last packet was sent.

A USB mouse uses a somewhat different communication protocol however the button, wheel and X/Y motion data transmitted by the mouse is the same and the data is packetized in a similar way. It is also possible for a USB mouse to be plugged into a PS/2 port, or a PS/2 mouse to be plugged into a USB port using commonly available adapter plugs.

When a computer mouse is connected to the ringlight 10, the mouse port emulator 42 performs all of the necessary PS/2 or USB protocol functions to communicate with the mouse, and provides data received from the mouse to other circuits. It provides the light source sequencer 34 with mouse button and wheel status, and provides raw X and Y mouse motion data to the device interpreter 38. Mouse button and wheel status is used by the light source sequencer 34 to set light sources intensity, set number of light sources that are illuminated, initiate automatic light source rotation for hands-free operation, set the rotation rate of automatic light source rotation, and the like. The function of the device interpreter circuit is to translate X and Y mouse motion into light source directional information which is then used by the light source sequencer 34 to steer the light source illumination in the desired direction. Four different translation algorithms are presented, each of which provides a different user interface.

First Algorithm

This is the preferred algorithm. It provides an intuitive user interface and requires no trigonometric or square root functions to implement. The mouse is moved by the user in a clockwise or counterclockwise circular motion to rotate the light source illumination in the corresponding clockwise or counterclockwise direction. This algorithm also gives the user a convenient and intuitive way to control light source rotation rate. The light source rotation rate is determined by the tangential velocity of the mouse, therefore larger diameter circular motion of the mouse gives a faster light source rotation rate, whereas smaller diameter circular motion of the mouse gives a slower light source rotation rate and more precise user control. The mouse rotation angle is not phase-locked with the light source illumination angle, meaning that one rotation of the mouse can result in, for example, two rotations of the light source illumination. This has the advantage of allowing the ringlight to be mounted at any rotation angle with respect to the user, thereby avoiding operator confusion due to reversed or off-angle mouse control.

Rotation direction is detected by comparing successive pairs of mouse movement readings, (X1,Y1) and (X2,Y2), noting the relative difference in direction angle. This could be accomplished by using an arc tangent trigonometric function to convert (X1,Y1) and (X2,Y2) to two direction angles, however, a simpler method is employed where the direction angle of the instantaneous mouse motion is determined to within an accuracy of 45 degrees by comparing the relative magnitude and sign of the X and Y data values. For example, referring to Table 1, if X is positive, Y is positive, and the absolute value of X is greater than the absolute value of Y, then the mouse motion direction angle falls within octant 1. Knowing the angle to within 45 degrees is sufficient to determine which way the mouse is rotating after only 90 degrees of mouse rotation. By watching successive (X,Y) mouse motion readings for a change in octant, it can be determined if the mouse rotation direction is clockwise or counterclockwise. If several successive readings (X1,Y1), (X2,Y2), (X3,Y3), etc. are all within the same octant, then it is assumed that mouse rotation has continued in the same direction. Only when a reading falls in another octant might it be discovered that the mouse rotation direction has changed. The rotation direction, clockwise or counterclockwise, is sent to the light source sequencer 34.

TABLE 1

Mouse data to octant conversion

| octant 0 | X = Positive | Y = Positive | |X| <= |Y| |
| octant 1 | X = Positive | Y = Positive | |X| > |Y| |
| octant 2 | X = Positive | Y = Negative | |X| > |Y| |
| octant 3 | X = Positive | Y = Negative | |X| <= |Y| |
| octant 4 | X = Negative | Y = Negative | |X| <= |Y| |
| octant 5 | X = Negative | Y = Negative | |X| > |Y| |
| octant 6 | X = Negative | Y = Positive | |X| > |Y| |
| octant 7 | X = Negative | Y = Positive | |X| <= |Y| |

This algorithm uses the tangential mouse velocity to determine the light source rotation rate. One way to derive the tangential velocity is to take the square-root of X squared plus Y squared, however, a far less computationally intensive method is used instead. Velocity is approximated as the absolute value of X or the absolute value of Y, whichever is greater. Therefore, if |X|>|Y| then the velocity is set to |X|. Conversely, if |X|<|Y| then the velocity is set to |Y|. This approximation method is indistinguishable from the square-root method as far as the user is concerned. This velocity information is sent to the light source sequencer circuit where it is used to set the rotation rate of the light source illumination.

Second Algorithm

Figure 6:
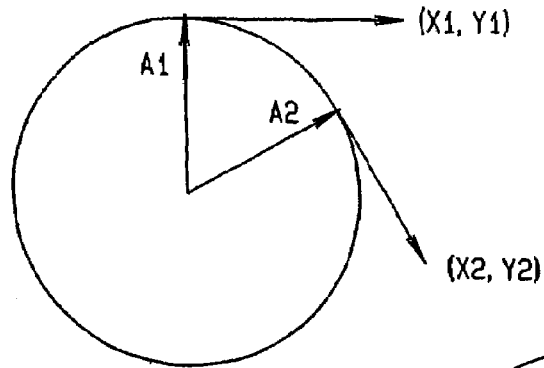
FIG. 6 is a diagram showing an algorithm for determining mouse movement in order to calculate illumination angle of the ringlight according to an embodiment of the present invention.

This algorithm has an advantage in that the mouse rotation angle is phase-locked with the light source rotation angle, therefore the user has a feel for the light source illumination direction based on the mouse position. Referring to FIG. 6, when mouse data (X1,Y1) is sampled, the mouse motion direction angle is computed as the arctangent of Y1 divided by X1 (atan(Y1/X1)), and the resultant light source illumination angle A1 is set to atan(Y1/X1)−90 degrees. On the next mouse data sample (X2,Y2), the calculation is repeated, giving a new light source illumination angle A2 equal to atan(Y2/X2)−90 degrees. One can see that the only information that need be sent to the light source sequencer 34 from the mouse rotation detection circuit is the current light source illumination angle. No rotation rate information need be provided to the light source sequencer 34 since the rate is established by the change in successive light source illumination angles.

This algorithm has a drawback in that if the mouse is being rotated very slowly or moved linearly by the user, then the light source illumination angle will be perceived by the user to be −90 degrees out of phase from the mouse movement.

Another drawback of this algorithm is the computationally intensive division and trigonometric functions required.

Yet another drawback of this algorithm is that the ringlight must be mounted at a specific rotation angle with respect to the user, or some means must be provided to add a rotation correction factor, otherwise the operator will be confused due to reversed or off-angle mouse control.

Third Algorithm

Figure 7:
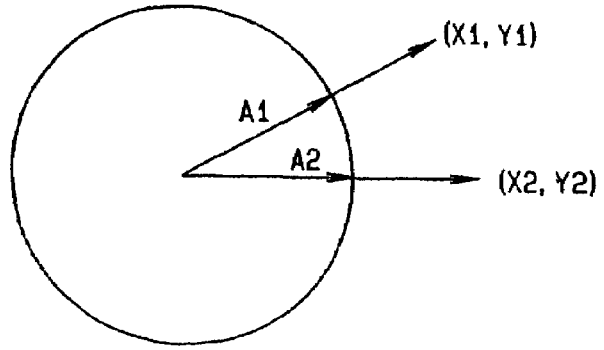
FIG. 7 is a diagram showing an algorithm for determining mouse movement in order to calculate illumination angle of the ringlight according to an embodiment of the present invention.

This algorithm is similar to the rotational, phase-locked algorithm but corrects for the problem of counter-intuitive operation when the mouse is being rotated very slowly or moved linearly by the user. A sliding phase correction factor of between 0 and +90 degrees is added to the light source illumination angle depending on the mouse rotation rate. Referring to FIG. 7, for very slow mouse rotation or linear mouse movement, the correction factor is +90 degrees, resulting in the light source rotation angle being equal to the mouse movement angle. For mouse rotation rates from near zero to some maximum rate the correction factor is adjusted proportionately from +90 degrees down to zero, so that above the maximum mouse rotation rate the light source illumination angle is −90 degrees out of phase with the mouse rotation angle as demonstrated graphically in FIG. 6. The resultant formula for the light source illumination angle A1 is atan(Y1/X1)−90+CF where CF is the above mentioned correction factor.

Similar to the second algorithm, this algorithm has the drawback of requiring computationally intensive division and trigonometric functions, and additionally requires the sliding phase correction computation.

As with the rotational, phase-locked algorithm, this algorithm also requires that the ringlight be mounted at a specific rotation angle with respect to the user, or some means provided to add a rotation correction factor, otherwise the operator will be confused due to reversed or off-angle mouse control.

Fourth Algorithm

Figure 8:
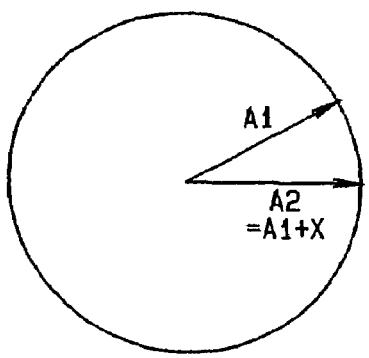
FIG. 8 is a diagram showing an algorithm for determining mouse movement in order to calculate illumination angle of the ringlight according to an embodiment of the present invention.
Figure 9:
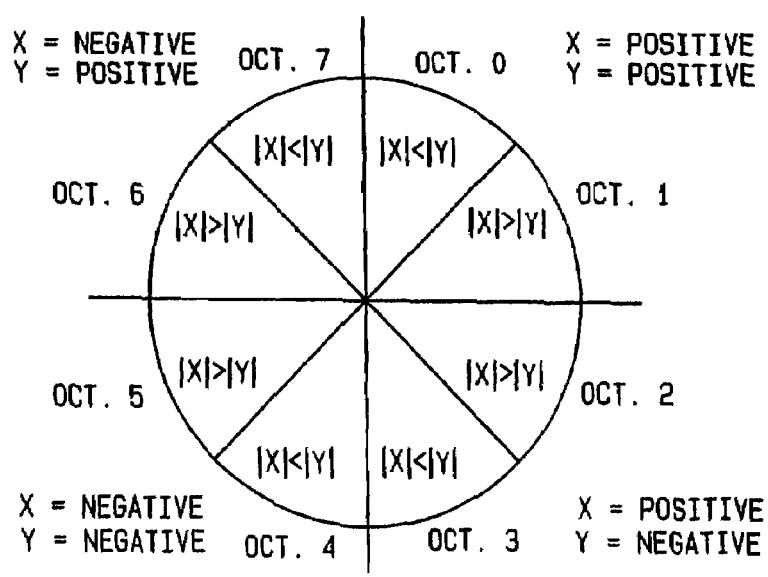
FIG. 9 is a diagram showing an algorithm for determining mouse movement in order to calculate illumination angle of the ringlight according to an embodiment of the present invention.

This algorithm is very simple but the operator interface is not as intuitive as in the previously discussed algorithms. Within this algorithm, the light source illumination angle is directly determined by the horizontal (X) motion of the mouse. Referring to FIG. 8, if the mouse is moved right in the +X direction, the light source illumination angle A1 is changed proportionately by +X degrees to angle A1+X=A2. If the mouse is moved left in the −X direction the light source illumination angle rotates proportionately in the opposite direction. The Y mouse axis can be used to control light source intensity, number of light sources illuminated, or the like. One can see that with this algorithm, the only information that need be sent to the light source sequencer 34 from the device interpreter 38 is the current light source illumination angle. No rotation rate information need be provided to the light source sequencer 34 from the device interpreter 38.

Note that if the operator holds the mouse at a slight angle, or has a tendency to move the mouse in non-perpendicular X and Y directions, then the X and Y controls will interact, producing unexpected light source illumination rotation or unexpected Y axis control changes. This problem is solved by comparing the magnitude of X and Y, and allowing only the larger value to take precedence. So, for example, if X changes by −5 and Y changes by +1 then an X (illumination rotation) change of −5 is made and no change is made in the Y control because |−5|>|+1|. This solution need only be applied where the Y mouse axis is utilized and if interaction between X and Y is not desirable.

Preferably, the preset modes available in the ringlight include a mode where three-fourths of the light sources are illuminated, a mode where one half of the light sources are illuminated, a mode where one-fourth of the light sources are illuminated, and a mode where only one light source was illuminated. Additionally, the preset modes can include preset locations for the illuminated light sources, for example, where one-fourth of the light sources are illuminated in a first mode, where one-fourth of the light sources are illuminated at a position 90 degrees from the first position, where one-fourth of the light sources are illuminated at a position 180 degrees from the first position, and where one-fourth of the light sources are illuminated at a position 270 degrees from the first position.

Optionally, a switch 50 can be provided to allow preset mode selection during periods when the externally-located hand manipulable user device 40 is not attached to the ringlight. In this manner, the switch 50 acts as an internally-located hand manipulable user device. While not in the preferred embodiment, it within the scope of the present invention to include some or all of the functionality of the mouse within the housing 12 of the ringlight 10 by adding additionally further functionality to the switch such as additional switches, a potentiometer or an encoder wheel, for example, to control the location and illumination of the light sources 30.

It is further within the scope of the present invention to, rather than select certain light sources to be either on or off, to select light sources to have varying illumination intensity at a location along the arrangement of light sources. For example, by moving a standard computer mouse, a user varies a location of highest intensity along the arrangement of light sources and by rolling the wheel of the mouse varies the gradient of illumination from the location of the highest illumination to a light source opposite the light source of highest illumination.

Additionally, while the printed circuit board is flat and the arrangement of light sources is a single circle in the preferred embodiment of the invention, it is within the scope of the present invention to provide other arrangements. For example, additional rings of light sources may be provided around the first ring with each ring of light sources converging on the same point. Moreover, the light sources can be arranged in a cylindrical pattern, i.e. multiple rings of light sources having the same diameter and placed about a central axis. Moreover, the light sources could be arranged in a conical arrangement or in a dome-shaped arrangement. Finally, the light sources could be arranged in conjunction with known arrangements of mirrors or prisms to redirect light.

Additionally, while it is contemplated that the hand manipulable user device is directly attached to the ringlight 10, it is also within the scope of the present invention that the hand manipulable user device be attached directly to computer which is, in turn, attached to the hand manipulable user device.

It is also contemplated that the present invention may contain a magnifying element rather than being attached to a separate magnifying element, such as by incorporating the device integrally within a known magnifying device, such as a magnifying glass or a microscope.

While the specific embodiments have been illustrated and described, numerous modifications come to mind without significantly departing from the spirit of the invention, and the scope of protection is only limited by the scope of the accompanying claims.

We claim:

1. An illumination device for a magnifying device comprising:
   a plurality of light sources to illuminate a specimen of the magnifying device;
   a user manipulable control that is adapted to detect relative motion of the control;
   a circuit for receiving an input from the user manipulable control, for determining an illumination angle of the plurality of light sources upon the magnifying device specimen based upon the input, and illuminating the magnifying device specimen with at least one of the light sources such that the light sources are illuminated in accordance with the illumination angle; and wherein the user manipulable control is adapted to detect when the control has been moved from a first physical location to a second physical location and the circuit adjusts the illumination angle upon the magnifying device specimen based upon the amount of detected relative movement of the control from the first location to the second location.

2. The illumination device of claim 1 wherein the user manipulable control is a mouse and the input to the circuit from the mouse indicates whether the mouse has been moved.

3. The illumination device of claim 2 wherein a rate of change in the illumination angle is determined by determining a tangential velocity of the mouse and a rotation direction of the illumination is determined by the clockwise or counterclockwise rotation of the mouse.

4. The illumination device of claim 2 wherein the illumination angle is determined by determining the mouse motion direction.

5. The illumination device of claim 2 wherein the illumination angle is determined by determining the mouse X motion or mouse Y motion.

6. The illumination device of claim 1 wherein the user manipulable control is a mouse and the illumination angle is determined by determining rotation of a mouse wheel.

7. The illumination device of claim 1 wherein the circuit receives a second input from the user manipulable control and the circuit further determines the number of light sources to be illuminated based upon the second input and illuminates the determined number of light sources.

8. The illumination device of claim 7 wherein the user manipulable control is a mouse and the second input to the circuit from the mouse indicates whether wheel of the mouse has been moved.

9. The illumination device of claim 7 wherein the circuit receives a third input from the user manipulable control, the circuit further determines the brightness of the light sources to be illuminated based upon the third input and illuminates the light sources to be illuminated to the desired brightness.

10. The illumination device of claim 1 wherein the light sources comprise light emitting diodes.

11. The illumination device of claim 1 wherein the light sources are arranged in a linear array.

12. The illumination device of claim 1 wherein the light sources are arranged in at least two concentric circles.

13. The illumination device of claim 1 wherein the circuit receives a second input from the user manipulable control and illuminates the light sources based upon a preset illumination pattern in response to the second input.

14. The illumination device of claim 1 wherein the circuit comprises a microprocessor.

15. An illumination device for a magnifying device comprising:
a plurality of light sources to illuminate a specimen of the magnifying device attached to a printed circuit board and disposed around an opening in the illumination device;
a user manipulable control selected from the group consisting of trackball, joystick, touch pad, wireless mouse, digitizing pad, or foot manipulated control; and
a circuit for receiving an input from the user manipulable control, for determining an illumination angle upon the magnifying device specimen based upon the input, and illuminating the magnifying device specimen with at least one of the light sources such that the light sources are illuminated in accordance with the illumination angle.

16. The illumination device of claim 15 wherein the user manipulable control is a mouse and the input to the circuit from the mouse indicates whether the mouse has been moved.

17. The illumination device of claim 16 wherein a rate of change in the illumination angle is determined by determining a tangential velocity of the mouse and a rotation direction of the illumination is determined by the clockwise or counterclockwise rotation of the mouse.

18. The illumination device of claim 15 wherein the illumination angle is determined by determining the mouse motion direction.

19. The illumination device of claim 15 wherein the illumination angle is determined by determining the mouse X motion or mouse Y motion.

20. The illumination device of claim 15 wherein the user manipulable control is a mouse and the illumination angle is determined by determining rotation of a mouse wheel.

21. The illumination device of claim 15 wherein the user manipulable control is a mouse and the circuit receives a second input from the mouse, the circuit further determines the number of light sources to be illuminated based upon the second input and illuminates the determined number of light sources.

22. The illumination device of claim 21 wherein the second input to the circuit from the mouse indicates whether wheel of the mouse has been moved.

23. The illumination device of claim 21 wherein the circuit receives a third input from the mouse, the circuit further determines the brightness of the light sources to be illuminated based upon the third input and illuminates the light sources to be illuminated to the desired brightness.

24. An illumination device for a magnifying device comprising:
a plurality of light sources to illuminate a specimen of the magnifying device disposed about an opening in the illumination device;
a mouse;
a circuit for determining movement of the mouse to control an illumination angle upon the magnifying device specimen of the plurality of light sources.

25. The illumination device of claim 24 wherein the circuit receives an input from the mouse indicating whether the wheel of the mouse has been moved, the circuit further determines the number of light sources to be illuminated based upon the movement of the wheel and illuminates the determined number of light sources.

26. The illumination device of claim 24 wherein the circuit receives an input from the mouse indicating whether a button has been pressed, the circuit further determines the brightness of the light sources to be illuminated based upon whether the button has been pressed and illuminates the light sources to be illuminated to the desired brightness.

27. The illumination device of claim 24 wherein the light sources are arranged in a generally circular arrangement.

28. The illumination device of claim 24 wherein the light sources are light emitting diodes.

* * * * *